United States Patent [19]

Fischer

[11] Patent Number: 5,453,535

[45] Date of Patent: Sep. 26, 1995

[54] PREPARATION OF α,ω-DICARBOXYLIC ACID DIESTERS

[75] Inventor: Rolf Fischer, Heidelberg, Germany

[73] Assignee: BASF Aktiengesellschaft, Ludwigshafen, Germany

[21] Appl. No.: 266,226

[22] Filed: Jun. 27, 1994

[30] Foreign Application Priority Data

Jul. 1, 1993 [DE] Germany ............. 43 21 842.3

[51] Int. Cl.[6] .................................. C07C 69/34
[52] U.S. Cl. .................. 560/190; 560/180; 560/181; 560/170; 560/171; 560/156
[58] Field of Search ................. 560/190, 181, 560/180, 156, 170, 171

[56] References Cited

U.S. PATENT DOCUMENTS 3,574,756 4/1971 Sheehan et al. .

FOREIGN PATENT DOCUMENTS 1668730 9/1971 Germany .
1206783 9/1970 United Kingdom .
1204905 9/1970 United Kingdom .

Primary Examiner—José G. Dees
Assistant Examiner—Samuel Barts
Attorney, Agent, or Firm—John H. Shurtleff

[57] ABSTRACT

A process for the preparation of a α,ω-dicarboxylic acid diester of the general formula I

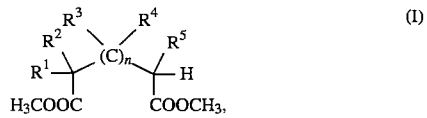

in which $R^1$, $R^2$, $R^3$, $R^4$, $R^5$ denotes hydrogen, $C_1$–$C_{20}$alkyl, $C_2$–$C_{20}$alkenyl, $C_2$–$C_{20}$alkynyl, $C_2$–$C_{20}$alkoxycarbonyl, nitro, $C_1$–$C_{20}$alkoxy and/or cyano and n is an integer from 1 to 12, wherein cycloalkanones of the general formula II

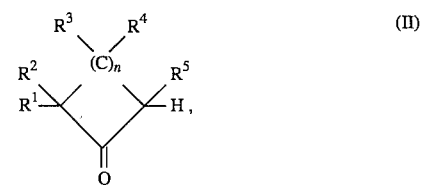

in which $R^1$, $R^2$, $R^3$, $R^4$, $R^5$ and n have the aforementioned meanings, are caused to react with dimethylcarbonate in the presence of a nitrogenous base of the general formula III

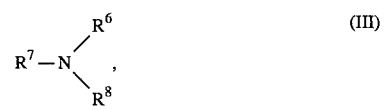

in which $R^6$, $R^7$, $R^8$ denote hydrogen, $C_1$–$C_{20}$alkyl, $C_3$–$C_8$cycloalkyl or $C_7$–$C_{20}$aralkyl or $R^6$ and $R^7$ together form a $C_2$–$C_7$alkylene chain optionally mono- to penta-substituted by $R^1$, at temperatures ranging from 50° to 300° C.

17 Claims, No Drawings

PREPARATION OF α,ω-DICARBOXYLIC ACID DIESTERS

The present invention relates to a process for the preparation of α,ω-dicarboxylic acid diesters by the reaction of cycloalkanones with dimethylcarbonate in the presence of nitrogen bases.

DE-A 1,668,730 reveals that it is possible to cause cycloalkanones to react with dialkyl carbonates in the presence of alcoholates or alkali metals. In this case, following purification with aqueous mineral acids, there are isolated α,ω-dicarboxylic acid diesters, which contain one carbon atom more than the cyclic starting ketones. The Examples 1 to 6 describe the reaction of cyclodecanone or cyclododecanone to produce nonanedicarboxylic acid diesters and undecanedicarboxylic acid diesters respectively. The process is carried out using amounts of alkali metal or alcoholate of one to one and a half moles per mole of cycloalkanone used in excess dialkyl carbonate as solvent.

This process thus suffers from the drawback of a high occurrence of mineral salts.

It was thus the object of the present invention to overcome said drawback.

Accordingly, we have found a novel and improved process for the preparation of α,ω-dicarboxylic acid diesters of the general formula I

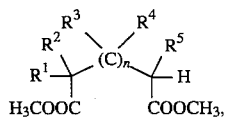

in which
$R^1$, $R^2$, $R^3$, $R^4$, $R^5$ denotes hydrogen, $C_1$–$C_{20}$alkyl, $C_2$–$C_{20}$alkenyl, $C_2$–$C_{20}$alkynyl, $C_2$–$C_{20}$alkoxycarbonyl, nitro, $C_1$–$C_{20}$alkoxy and/or cyano and n is an integer from 1 to 12,
wherein cycloalkanones of the general formula II

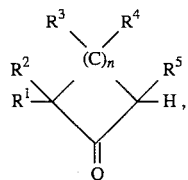

in which
$R^1$, $R^2$, $R^3$, $R^4$, $R^5$ and n have the aforementioned meanings, are caused to react with dimethylcarbonate in the presence of a nitrogenous base of the general formula III

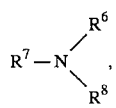

in which
$R^6$, $R^7$, $R^8$ denote hydrogen, $C_1$–$C_{20}$alkyl, $C_3$–$C_8$cycloalkyl or $C_7$–$C_{20}$aralkyl or $R^6$ and $R^7$ together form a $C_2$–$C_7$alkylene chain optionally mono- to penta-substituted by $R^1$,
at temperatures ranging from 50° to 300° C.

The process of the invention can be carried out as follows:

The cycloalkanones II can be brought together with dimethylcarbonate in the presence of nitrogenous bases III, eg, in pressure equipment and the reaction can be carried out at temperatures ranging from 50° to 300° C., preferably from 100° to 250° C. and more preferably from 150° to 230° C. and pressures of from 0.01 to 50 bar, preferably from 0.5 to 5 bar and more preferably under the pressure which is automatically built up in the respective reaction mixture.

The reaction can be carried out in the gas phase, but preferably in the liquid phase, batchwise or continuously.

It may be advantageous to carry out the reaction in the presence of gases inert under the reaction conditions, such as nitrogen or argon.

The reaction of the cycloalkanones II in the liquid phase can be carried out, for example, by heating a mixture of II and, optionally, a solvent to the desired temperature of reaction in the presence of dimethylcarbonate and the nitrogenous bases III. On completion of the reaction, the reaction mixture can be cooled and fractionally distilled in order to isolate the desired α,ω-dicarboxylic acid diesters.

The reaction of the invention can be carried out in the absence of solvents. However it may be advantageous to operate in the presence of inert solvents. Examples of suitable inert solvents for use in the process are acyclic or cyclic ethers such as diethyl ether, tetrahydrofuran and dioxane, aromatics, eg, benzene, toluene and the xylenes, chlorinated hydrocarbons such as chloroform and methylene chloride.

The amount of solvent is, based on the cycloalkanones I used, from 0 to 90 wt %, preferably from 5 to 80 wt % and more preferably from 20 to 60 wt %.

The molar ratio of cycloalkanone II to the dimethylcarbonate is usually from 10:1 to 1:1, and preferably from 5:1 to 2:1. An alternative possibility is to operate in excess dimethylcarbonate as solvent.

Suitable nitrogenous bases III are ammonia, primary, secondary and tertiary amines with aliphatic, cycloaliphatic, heteroaromatic, and/or araliphatic substituents or mixtures of such nitrogenous bases. Alternatively, two aliphatic substituents can be closed to form a ring. Diamines are also suitable.

Examples thereof are:
ammonia,
methylamine, ethylamine, hexylamine and cyclohexylamine,
dimethylamine, diethylamine, dibutylamine and dicyclohexylamine,
trimethylamine, dimethylethylamine, triethylamine, tri-n-propylamine, triisopropylamine, tributylamine, trioctylamine, tricyclohexylamine, trihexadecylamine, tricyclohexylamine, diphenylmethylamine, dimethylbenzlamine, dibenzylmethylamine, tribenzylamine, N,N-tetramethylhexamethylenediamine, hexamethylene diamine and tetramethylenediamine,
4-dimethylaminopyridine, urotropine, piperidine, N-methylpiperidine, pyrrolidine, N-methylpyrrolidine, hexamethyleneimine, N-ethylhexamethyleneimine, N-methylimidazole, 1,4-diazabicyclo[4.3.0]octane (DABCO), morpholine, piperazine and pyrrolidine.

Furthermore, amidines such as 1,5-diazabicyclo[4.3.0] non-5-ene (DBN), 1,8-diazabicyclo[5.4.0] undec-7-ene (DBU) and guanidine are suitable. The tertiary amines are preferred and more preferably $C_1$–$C_8$trialkylamines.

The molar ratio of cycloalkanone II to the nitrogenous bases is usually from 100:1 to 1:1, and preferably from 20:1 to 3:1.

Cycloalkanones II used as starting compounds are generally available compounds, which are manufacturable, eg, as described in Houben-Weyl, *Methoden der Organischen Chemie,* 4th Edition, Vol. VII/2a, pp. 637–641 and 699–711 (1973).

Examples of such cycloalkanones II are cyclopentanone, cylcohexanone, cylcoheptanone, cyclooctanone, cyclododecanone, 2-methylcyclopentanone, 2-ethylcyclohexanone, 2,5-dimethylcyclopentanone, 2-cyanocyclohexanone, 2-nitrocyclohexanone, 2-nitrocyclopentanone, 2-methylcyclooctanone, 2-methoxycarbonylcyclohexanone, 2-vinylcyclohexanone, 2,6-dimethylcyclohexanone, 2-methoxycyclohexanone.

The substituents $R^1$, $R^2$, $R^3$, $R^4$, $R^5$, $R^6$, $R^7$, $R^8$ and the index n in the compounds I, II and Ill have the following meanings:

$R^1, R^2, R^3, R^4, R^5, R^6, R^7, R^8$ hydrogen, $C_1$–$C_{20}$alkyl, preferably $C_1$–$C_8$alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, n-heptyl, isoheptyl, n-octyl, isooctyl and more preferably $C_1$–$C_4$alkyl such as methyl, ethyl, n-propyl, isopropyl, n-butyl, isobutyl, sec-butyl and tert-butyl, $R^1, R^2, R^3, R^4, R^5$ $C_2$–$C_{20}$alkenyl, preferably $C_2$–$C_8$alkenyl such as vinyl, allyl, but-2-en-1 -yl, but-4 -en-1-yl, but-4-en-2-yl, pent-2-en-1-yl, 2,2-dimethyl-pent-1-en-1-yl, $C_2$–$C_{20}$alkynyl, preferably $C_2$–$C_8$alkynyl and more preferably $C_2$–$C_4$alkynyl such as ethynyl, 1-propynyl, 2-propynyl, 1-butynyl, 2-butynyl, 3-butynyl, 1-methyl-2-propynyl, $C_2$–$C_{20}$alkoxycarbonyl, preferably $C_2$–$C_9$alkoxycarbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, isopentoxycarbonyl, sec-pentoxycarbonyl, neopentoxycarbonyl, 1,2-dimethylpropoxycarbonyl, n-hexoxycarbonyl, isohexoxycarbonyl, sec-hexoxycarbonyl, n-heptoxycarbonyl, isoheptoxycarbonyl, n-octoxycarbonyl and isooctoxycarbonyl and more preferably $C_1$–$C_5$alkoxycarbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, nitro, $C_1$–$C_{20}$alkoxy, preferably $C_1$–$C_8$alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy and isooctoxy and more preferably $C_1$–$C_4$alkoxy such as methoxy, ethoxy, n-propoxy, isopropoxy, n-butoxy, isobutoxy, sec-butoxy, tert-butoxy, cyano and $R^6, R^7, R^8$ $C_3$–$C_8$cycloalkyl such as cyclopropyl, cyclobutyl, cyclopentyl, cyclohexyl, cycloheptyl and cyclooctyl, preferably cyclopentyl, cyclohexyl and cyclooctyl and more preferably cyclopentyl and cyclohexyl, $C_7$–$C_{20}$aralkyl, preferably $C_7$–$C_{12}$phenylalkyl such as benzyl, 1-phenethyl, 2-phenethyl, 1-phenylpropyl, 2-phenylpropyl, 3-phenyl-propyl, 1-phenylbutyl, 2-phenylbutyl, 3-phenylbutyl and 4-phenylbutyl and more preferably benzyl, 1-phenethyl and 2-phenethyl or $R^6$ and $R^7$ together can form a $C_2$–$C_7$alkylene chain optionally mono- to penta-substituted by $R^1$ such as ethylene, propylene, butylene and pentylene, preferably butylene and pentylene, n an integer from 1 to 12, preferably an integer from 2 to 9 and more preferably an integer from 2 to 5, in particular 2 or 3.

EXAMPLES

EXAMPLE 1

A mixture of 22.4 g of 2,5-dimethylcyclopentanone, 45 g of dimethylcarbonate, and 3 g of ethyldimethylamine was heated to 200° C. in an autoclave and stirred for 5 hours at this temperature. Following cooling of the autoclave, the liquid effluent was fractionally distilled. There were thus obtained 7.4 g of unconverted 2,5-dimethylcyclopentanone (33%, based on 2,5-dimethylcyclopentanone used) and 17.4 g of dimethyl 2,5-dimethyladipate (yield 43%, based on 2,5-dimethylcyclopentanone used, selectivity 64% ).

EXAMPLE 2

A mixture of 24.5 g of cyclohexanone, 115 g of dimethylcarbonate, and 3.7 g of ethyldimethylamine was caused to react as described in Example 1. Gas chromatographic analysis (GC % by area) demonstrated that the effluent (without unconverted dimethylcarbonate and without methanol formed) consisted of 19% of unconverted cyclohexanone, 35% of dimethyl pimelate, and 10% of dimethyl 2-methyl pimelate.

EXAMPLE 3

Example 2 was repeated except that ethyl cyclohexanone-2-carboxylate was used instead of cyclohexanone as starting product, a mixture of dimethyl pimelate and methylethyl pimelate was identified as main product.

EXAMPLE 4

A mixture of 9.8 g of 2-methylcyclopentanone, 45.9 g of dimethylcarbonate, and 1.20 g of triethylamine was caused to react as described in Example 1. Gas chromatographic analysis (GC % by area) demonstrated that the effluent contained as main products, in addition to unconverted ketone, dimethylcarbonate and the methanol formed, dimethyl 2-methyladipate and dimethyl 2,5-dimethyladipate in a molar ratio of 1:1.3.

We claim:

1. A process for the preparation of an α,ω-dicarboxylic acid diester of the formula

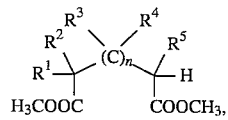

in which each of $R^1$, $R^2$, $R^3$, $R^4$ and $R^5$ independently denotes hydrogen, $C_1$–$C_{20}$-alkyl, $C_2$–$C_{20}$-alkenyl, $C_2$–$C_{20}$-alkynyl, $C_2$–$C_{20}$-alkoxycarbonyl, nitro, $C_1$–$C_{20}$-alkoxy or cyano, and n is an integer of from 1 to 12, said process comprising:

bringing together a reaction mixture consisting of
(A) a cycloalkanone of the formula

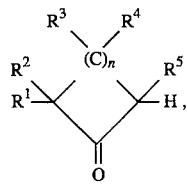

in which $R^1$, $R^2$, $R^3$, $R^4$, $R^5$ and n have the meanings given above;
(B) dimethylcarbonate; and
(C) a nitrogenous base of the formula

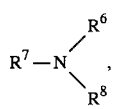

in which each of $R^6$, $R^7$, and $R^8$ independently denotes hydrogen, $C_1$–$C_{20}$-alkyl, $C_3$–$C_{20}$-cycloalkyl or $C_7$–$C_{20}$-aralkyl, or $R^6$ and $R^7$ when taken together form a $C_2$–$C_7$-alkylene chain optionally mono- to penta-substituted by $R^1$,
and reacting said mixture, optionally in the presence of an inert solvent, at a temperature ranging from 50° to 300° C. and under a pressure of from 0.01 to 50 bar.

2. A process for the preparation of a α,ω-dicarboxylic acid diester I as defined in claim 1, wherein the nitrogenous base used comprises 1,5-diazabicyclo[4.3.0]non-5-ene and 1,8-diazabicyclo[5.4.0]undec-7-ene.

3. A process for the preparation of a α,ω-dicarboxylic acid diester I as defined in claim 1, wherein the cycloalkanone II is used in a molar ratio to the nitrogenous base of from 100:1 to 1:1.

4. A process for the preparation of a α,ω-dicarboxylic acid diester I as defined in claim 1, wherein the reaction is carried out at temperatures ranging from 100° to 250° C.

5. A process for the preparation of a α,ω-dicarboxylic acid diester I as defined in claim 1, wherein the reaction is carried out at temperatures ranging from 150° to 230° C.

6. A process for the preparation of a α,ω-dicarboxylic acid diester I as defined in claim 1, wherein the reaction is carried out in a pressure reactor under autogenous pressure.

7. A process as claimed in claim 1, wherein the reaction is carried out under a pressure of from 0.5 to 5 bar.

8. A process as claimed in claim 1, wherein the cycloalkanone II is used in a molar ratio to the nitrogenous base of from 20:1 to 3:1.

9. A process as claimed in claim 1, wherein the cycloalkanone II is used in a molar ratio to the dimethylcarbonate of from 10:1 to 1:1.

10. A process as claimed in claim 1, wherein the cycloalkanone II is used in a molar ratio to the dimethylcarbonate of from 5:1 to 2:1.

11. A process as claimed in claim 1, wherein the nitrogenous base is a tertiary amine.

12. A process as claimed in claim 1, wherein the nitrogenous base is a tertiary amine selected from the group consisting of trimethylamine, dimethylethylamine, triethylamine, tri-n-propylamine, tri-isopropylamine and tributylamine.

13. A process as claimed in claim 1, wherein the reaction is carried out in the presence of up to 90% by weight of an inert solvent, based on the cycloalkanone II.

14. A process as claimed in claim 1, wherein the reaction is carried out in the presence of from 20 to 60% by weight of an inert solvent, based on the cycloalkanone II.

15. A process as claimed in claim 1, wherein the cycloalkanone II is 2,5-dimethylcyclopentanone.

16. A process as claimed in claim 1, wherein the cycloalkanone II is cyclohexanone.

17. A process as claimed in claim 1, wherein the cycloalkanone II is 2-methylcyclopentanone.

* * * * *